United States Patent
Chong

(10) Patent No.: US 11,213,200 B2
(45) Date of Patent: Jan. 4, 2022

(54) TOPOGRAPHICAL IMAGING USING COMBINED SENSING INPUTS

(71) Applicant: SANTEC CORPORATION, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 127 days.

(21) Appl. No.: 15/928,827

(22) Filed: Mar. 22, 2018

(65) Prior Publication Data

US 2019/0290123 A1    Sep. 26, 2019

(51) Int. Cl.
| | |
|---|---|
| *A61B 3/14* | (2006.01) |
| *A61B 3/10* | (2006.01) |
| *G01B 9/02* | (2006.01) |
| *H01S 5/14* | (2006.01) |
| *G01N 21/47* | (2006.01) |

(52) U.S. Cl.
CPC ............ *A61B 3/102* (2013.01); *A61B 3/1005* (2013.01); *G01B 9/02091* (2013.01); *G01N 21/4795* (2013.01); *H01S 5/141* (2013.01)

(58) Field of Classification Search
CPC ....... A61B 3/102; A61B 3/1005; A61B 3/103; A61B 5/0066; A61B 5/0073; A61B 5/0064; A61B 5/0086; A61B 2562/0242; G01B 9/02091; G01B 9/02004; G01B 9/0203; G01B 9/02027; G01B 9/02028; G01B 11/2441; G01B 11/002; G01B 2290/45
USPC ............... 351/206, 212, 221, 246; 356/450
See application file for complete search history.

(56) References Cited

U.S. PATENT DOCUMENTS

| | | | |
|---|---|---|---|
| 4,466,699 A | 8/1984 | Droessler et al. | |
| 5,022,745 A | 6/1991 | Zayhowski et al. | |
| 5,319,668 A | 6/1994 | Luecke | |
| 5,372,135 A | 12/1994 | Mendelson et al. | |
| 5,430,574 A | 7/1995 | Tehrani | |
| 5,491,524 A * | 2/1996 | Hellmuth ............... | A61B 3/102 351/205 |
| 5,537,162 A | 7/1996 | Hellmuth et al. | |
| 5,561,523 A | 10/1996 | Blomberg et al. | |
| 5,979,760 A | 11/1999 | Freyman et al. | |
| 5,982,963 A | 11/1999 | Feng et al. | |

(Continued)

FOREIGN PATENT DOCUMENTS

| | | |
|---|---|---|
| DE | 10 2011 114 797 A1 | 4/2013 |
| JP | 2006-202543 A | 8/2006 |

(Continued)

OTHER PUBLICATIONS

Final Office Action on U.S. Appl. No. 15/139,579 dated May 15, 2019.

(Continued)

*Primary Examiner* — Mahidere S Sahle
(74) *Attorney, Agent, or Firm* — Foley & Lardner LLP

(57) ABSTRACT

An OCT system is arranged to capture a three-dimensional (3D) OCT scan of a target. The OCT system projects a beam scan towards the target, and the OCT system generates data corresponding to the beam scan. Additionally, an image sensor is arranged to capture an image of a trace of the beam scan on a surface of the target. Using the image of the trace, various characteristics of the target are determined.

19 Claims, 4 Drawing Sheets

(56) References Cited

U.S. PATENT DOCUMENTS

| | | | |
|---|---|---|---|
| 6,070,093 A | 5/2000 | Oosta et al. |
| 6,111,645 A | 8/2000 | Tearney et al. |
| 6,134,003 A | 10/2000 | Tearney et al. |
| 6,160,826 A | 12/2000 | Swanson et al. |
| 6,275,718 B1 | 8/2001 | Lempert |
| 6,282,011 B1 | 8/2001 | Tearney et al. |
| 6,373,632 B1 | 4/2002 | Flanders |
| 6,421,164 B2 | 7/2002 | Tearney et al. |
| 6,485,413 B1 | 11/2002 | Boppart et al. |
| 6,501,551 B1 | 12/2002 | Tearney et al. |
| 6,556,853 B1 | 4/2003 | Cabib et al. |
| 6,564,087 B1 | 5/2003 | Pitris et al. |
| 6,725,073 B1 | 4/2004 | Motamedi et al. |
| 7,099,358 B1 | 8/2006 | Chong |
| 7,231,243 B2 | 6/2007 | Tearney et al. |
| 7,323,680 B2 | 1/2008 | Chong |
| 7,324,214 B2 | 1/2008 | De Groot et al. |
| 7,352,783 B2 | 4/2008 | Chong |
| 7,382,809 B2 | 6/2008 | Chong et al. |
| 7,388,891 B2 | 6/2008 | Uehara et al. |
| 7,400,410 B2 | 7/2008 | Baker et al. |
| 7,414,779 B2 | 8/2008 | Huber et al. |
| 7,428,057 B2 | 9/2008 | De Lega et al. |
| 7,489,713 B2 | 2/2009 | Chong et al. |
| 7,701,588 B2 | 4/2010 | Chong |
| 7,725,169 B2 | 5/2010 | Boppart et al. |
| 7,835,010 B2 | 11/2010 | Morosawa et al. |
| 7,865,231 B2 | 1/2011 | Tearney et al. |
| 7,869,057 B2 | 1/2011 | De Groot |
| 7,884,945 B2 | 2/2011 | Srinivasan et al. |
| 7,961,312 B2 | 6/2011 | Lipson et al. |
| 8,036,727 B2 | 10/2011 | Schurman et al. |
| 8,115,934 B2 | 2/2012 | Boppart et al. |
| 8,315,282 B2 | 11/2012 | Huber et al. |
| 8,405,834 B2 | 3/2013 | Srinivasan et al. |
| 8,427,649 B2 | 4/2013 | Hays |
| 8,500,279 B2 | 8/2013 | Everett et al. |
| 8,625,104 B2 | 1/2014 | Izatt et al. |
| 8,690,328 B1 | 4/2014 | Chong |
| 9,163,930 B2 | 10/2015 | Buckland et al. |
| 9,335,154 B2 | 5/2016 | Wax et al. |
| 9,851,433 B2 | 12/2017 | Sebastian |
| 2001/0034478 A1 | 10/2001 | Lambert et al. |
| 2002/0163948 A1 | 11/2002 | Yoshida et al. |
| 2004/0036838 A1 | 2/2004 | Podoleanu et al. |
| 2004/0257581 A1* | 12/2004 | Hogan ............... A61B 5/0059 |
| | | | 356/484 |
| 2005/0171438 A1 | 8/2005 | Chen et al. |
| 2005/0201432 A1 | 9/2005 | Uehara et al. |
| 2005/0213103 A1 | 9/2005 | Everett et al. |
| 2006/0105209 A1 | 5/2006 | Thyroff et al. |
| 2006/0109872 A1 | 5/2006 | Sanders |
| 2006/0215713 A1 | 9/2006 | Flanders et al. |
| 2007/0040033 A1 | 2/2007 | Rosenberg |
| 2007/0076217 A1 | 4/2007 | Baker et al. |
| 2007/0081166 A1 | 4/2007 | Brown et al. |
| 2007/0133647 A1 | 6/2007 | Daiber |
| 2007/0141418 A1 | 6/2007 | Ota et al. |
| 2007/0263226 A1 | 11/2007 | Kurtz et al. |
| 2007/0291277 A1 | 12/2007 | Everett et al. |
| 2008/0097194 A1 | 4/2008 | Milner |
| 2008/0269575 A1 | 10/2008 | Iddan |
| 2009/0022181 A1 | 1/2009 | Atkins et al. |
| 2009/0079993 A1 | 3/2009 | Yatagai et al. |
| 2009/0103050 A1 | 4/2009 | Michaels et al. |
| 2009/0169928 A1 | 7/2009 | Nishimura et al. |
| 2009/0247853 A1 | 10/2009 | Debreczeny |
| 2009/0268020 A1 | 10/2009 | Buckland et al. |
| 2009/0290613 A1 | 11/2009 | Zheng et al. |
| 2010/0110171 A1 | 5/2010 | Satake |
| 2010/0157308 A1 | 6/2010 | Xie |
| 2010/0246612 A1 | 9/2010 | Shimizu |
| 2010/0253908 A1 | 10/2010 | Hammer et al. |
| 2010/0284021 A1 | 11/2010 | Hacker |
| 2011/0080561 A1* | 4/2011 | Hayashi ............... A61B 3/102 |
| | | | 351/206 |
| 2011/0112385 A1 | 5/2011 | Aalders |
| 2011/0228218 A1 | 9/2011 | Hauger et al. |
| 2011/0235045 A1 | 9/2011 | Koerner |
| 2011/0255054 A1 | 10/2011 | Hacker et al. |
| 2011/0299034 A1 | 12/2011 | Walsh et al. |
| 2012/0013849 A1 | 1/2012 | Podoleanu et al. |
| 2012/0026466 A1 | 2/2012 | Zhou et al. |
| 2012/0133950 A1 | 5/2012 | Suehira et al. |
| 2012/0136259 A1 | 5/2012 | Milner et al. |
| 2012/0188555 A1 | 7/2012 | Izatt et al. |
| 2013/0265545 A1 | 10/2013 | Buckland et al. |
| 2014/0051952 A1 | 2/2014 | Reichgott et al. |
| 2014/0055749 A1* | 2/2014 | Zhou ............... A61B 3/0025 |
| | | | 351/214 |
| 2014/0111774 A1 | 4/2014 | Komine |
| 2014/0228681 A1 | 8/2014 | Jia et al. |
| 2014/0268163 A1 | 9/2014 | Milner et al. |
| 2014/0293290 A1 | 10/2014 | Kulkarni |
| 2014/0336479 A1 | 11/2014 | Ando |
| 2015/0223681 A1 | 8/2015 | Kuranov et al. |
| 2015/0342508 A1 | 12/2015 | Chong |
| 2015/0348287 A1 | 12/2015 | Yl et al. |
| 2016/0178346 A1 | 6/2016 | Kulkarni |
| 2016/0183780 A1* | 6/2016 | Docherty ............ G02B 27/0093 |
| | | | 351/206 |
| 2016/0324593 A1* | 11/2016 | El-Haddad ............... G06T 7/73 |
| 2017/0090031 A1 | 3/2017 | Bondy et al. |
| 2018/0088236 A1 | 3/2018 | Eichenholz et al. |
| 2018/0128594 A1 | 5/2018 | Lee et al. |

FOREIGN PATENT DOCUMENTS

| | | |
|---|---|---|
| JP | 2008-188047 A | 8/2008 |
| JP | 2010-172538 A | 8/2010 |
| WO | WO-2012/075126 A2 | 6/2012 |
| WO | WO-2013/168149 A1 | 11/2013 |
| WO | WO-2015/121756 A2 | 8/2015 |
| WO | WO-2017/176901 A1 | 10/2017 |

OTHER PUBLICATIONS

Final Office Action on U.S. Appl. No. 15/630,654 dated Sep. 12, 2018.

International Search Report and Written Opinion in PCT/US2019/027671 dated Jul. 1, 2019.

Non-Final Office Action on U.S. Appl. No. 14/723,325 dated Jan. 29, 2019.

Non-Final Office Action on U.S. Appl. No. 15/611,515 dated Oct. 5, 2018.

Notice of Allowance on U.S. Appl. No. 15/086,520 dated Jul. 9, 2019.

Notice of Allowance on U.S. Appl. No. 15/578,421 dated May 1, 2019.

Notice of Allowance on U.S. Appl. No. 15/611,515 dated May 21, 2019.

Notice of Allowance on U.S. Appl. No. 15/630,654 dated Apr. 22, 2019.

Notice of Allowance on U.S. Appl. No. 15/648,239 dated Oct. 30, 2018.

U.S. Office Action on U.S. Appl. No. 14/723,325 dated Apr. 19, 2019.

Chong, et al. "Large Coherence Length Swept Source for Axial Length Measurement of the Eye," Applied Optics, 2009, pp. D145-D150, vol. 48, Issue 10.

Chowdhury, et al., "Challenges & Countermeasures in Optical Noninvasive Blood Glucose Detection," International Journal of Innovative Research in Science, Engineering and Technology, Jan. 2013, pp. 329-334, vol. 2, Issue 1.

Dai, et al., "Optical coherence tomography for whole eye segment imaging," Optics Express, Mar. 2012, pp. 6109-6115, vol. 20, Issue 6.

Dhalla, et al., "Simultaneous swept source optical coherence tomography of the anterior segment and retina using coherence revival," Optics Letters, 2012, pp. 1883-1885, vol. 37, No. 11.

(56) References Cited

OTHER PUBLICATIONS

Fainman, et al., "Nanophotonics for Information Systems," Information Optics and Photonics, Oct. 1, 2010, pp. 13-37, T. Fournel and B. Javidi eds., Springer New York.
Final Rejection Office Action on U.S. Appl. No. 14/641,200 dated Dec. 7, 2015 (13 pages).
Final Rejection Office Action on U.S. Appl. No. 14/723,325 dated Apr. 24, 2017 (8 pages).
International Preliminary Report on Patentability on International Application No. PCT/IB2015/000808 dated Aug. 4, 2016 (7 pages).
International Preliminary Report on Patentability on International Application No. PCT/US2015/019299 dated Sep. 13, 2016 (8 pages).
International Preliminary Report on Patentability on International Application No. PCT/US2015/032727 dated Dec. 8, 2016 (7 pages).
International Preliminary Report on Patentability on International Application No. PCT/US2016/035012 dated Dec. 14, 2017 (11 pages).
International Search Report and Written Opinion dated Aug. 26, 2015 for PCT/US15/32727 (8 pages).
International Search Report and Written Opinion on International Application No. PCT/IB2015/000808 dated Oct. 20, 2015 (12 pages).
International Search Report and Written Opinion on International Application No. PCT/US2015/19299 dated Nov. 2, 2015(10 pages).
International Search Report and Written Opinion on International application No. PCT/US2016/035012 dated Aug. 18, 2016 (13 pages).
Jeong, et al., "Spectral-domain OCT with dual illumination and interlaced detection for simultaneous anterior segment and retina imaging," Optics Express, Aug. 2012, pp. 19148-19159, vol. 20, Issue 17.
Jia, et al., "Split-Spectrum Amplitude-Decorrelation Angiography with Optical Coherence Tomography," Optics Express, Feb. 2012, pp. 4710-4725, vol. 20 No. 4.
Lexer, et al., "Wavelength-tuning interferometry of intraocular distances," Applied Optics, 1997, pp. 6548-6553, vol. 36, Issue 25.
Mariampillai, et al., "Speckle Variance Detection of Microvasculature Using Swept-Source Optical Coherence Tomography," Optics Letters, Jul. 2008, pp. 1530-1532, vol. 33 No. 13.
Nankivil, et al., "Handheld, rapidly switchable, anterior/posterior segment swept source optical coherence tomography probe," Biomedical Optics Express, Nov. 2015, pp. 4516-4528, vol. 6, Issue 11.
Non-Final Office Action on U.S. Appl. No. 14/641,200 dated Aug. 19, 2015 (12 pages).
Non-Final Rejection Office Action on U.S. Appl. No. 13/892,997 dated Sep. 12, 2013 (15 pages).
Non-Final Rejection Office Action on U.S. Appl. No. 14/601,945 dated Mar. 2, 2016 (13 pages).
Non-Final Rejection Office Action on U.S. Appl. No. 14/613,644 dated Jun. 8, 2016 (8 pages).
Non-Final Rejection Office Action on U.S. Appl. No. 14/641,200 dated Mar. 14, 2016 (13 pages).
Non-Final Rejection Office Action on U.S. Appl. No. 14/723,325 dated Nov. 18, 2016 (8 pages).
Non-Final Rejection Office Action on U.S. Appl. No. 14/723,325 dated Dec. 7, 2017 (11 pages).
Non-Final Rejection Office Action on U.S. Appl. No. 15/202,925 dated Jul. 27, 2017 (8 pages).
Notice of Allowance on U.S. Appl. No. 13/892,997 dated Dec. 6, 2013 (9 pages).
Notice of Allowance on U.S. Appl. No. 14/601,945 dated Sep. 13, 2016 (10 pages).
Notice of Allowance on U.S. Appl. No. 14/613,644 dated Nov. 7, 2016 7 pages).
Notice of Allowance on U.S. Appl. No. 14/613,644 dated Nov. 18, 2016 (4 pages).
Notice of Allowance on U.S. Appl. No. 14/641,200 dated Jul. 12, 2016 (10 pages).
Notice of Allowance on U.S. Appl. No. 15/202,925 dated Feb. 13, 2018 (9 pages).
Ortiz, et al., "Corneal Topography From Spectral Optical Coherence Tomography (sOCT)," Biomedical Optics Express, Dec. 2011, pp. 3232-3247, vol. 2, No. 12.
Poddar, et al., "Non-Invasive Glucose Monitoring Techniques: A Review and Current Trends," Oct. 2008, pp. 1-47.
Sarlet, et al., "Wavelength and Mode Stabilization of Widely Tunable SG-DBR and SSG-DBR Lasers," IEEE Photonics Technology Letters, Nov. 1999, pp. 1351-1353, vol. 11, Issue 11.
Segawa, et al., "Semiconductor Double-Ring-Resonator-Coupled Tunable Laser for Wavelength Routing," IEEE Journal of Quantum Electronics, Jul. 2009, pp. 892-899, vol. 45, Issue 7.
Tayebati, et al., "Microelectromechanical tunable filter with stable half symmetric cavity," Electronics Letters, Oct. 1998, pp. 1967-1968, vol. 34, Issue 20.
Chopra et al., Topographical Thickness of the Skin in the Human Face, Aesthetic Surgery Journal, vol. 35(8), 2015, pp. 1007-1013.
Final Office Action on U.S. Appl. No. 14/723,325 dated Jul. 26, 2018.
Non-Final Office Action on U.S. Appl. No. 15/086,520 dated Aug. 6, 2018.
Non-Final Office Action on U.S. Appl. No. 15/139,579 dated Jul. 17, 2018.
Non-Final Office Action on U.S. Appl. No. 15/648,239 dated Jun. 6, 2018.
U.S. Notice of Allowance on U.S. Appl. No. 15/202,925 dated May 17, 2018.
U.S. Office Action on U.S. Appl. No. 15/630,654 dated Apr. 4, 2018.

\* cited by examiner

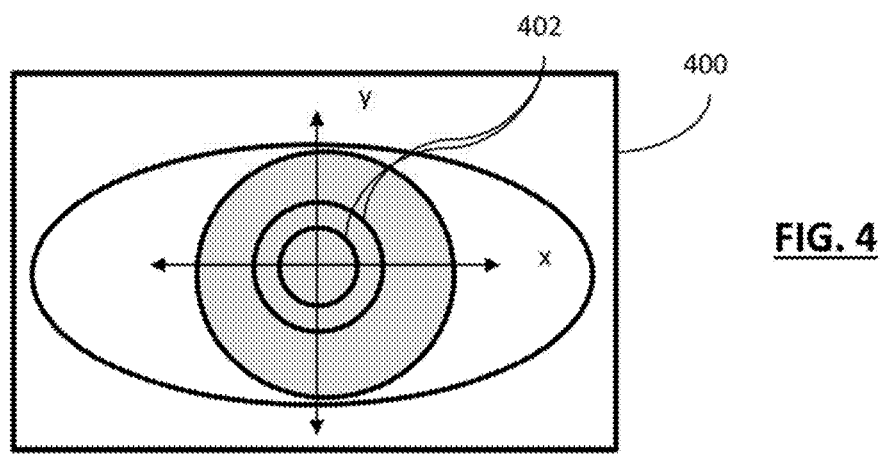
FIG. 4
FIG. 5
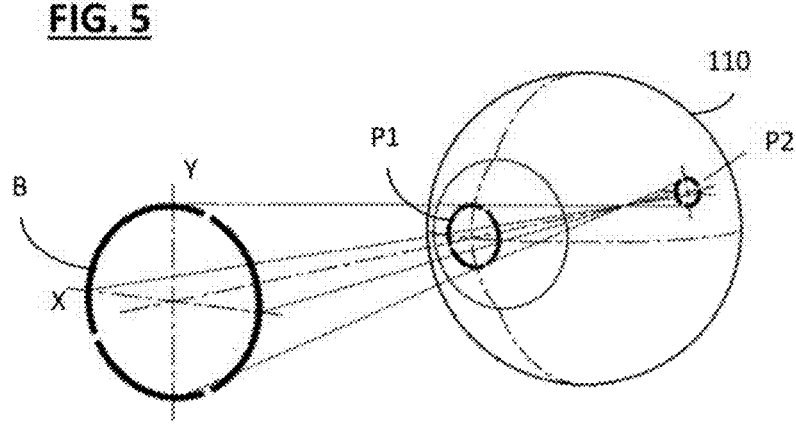
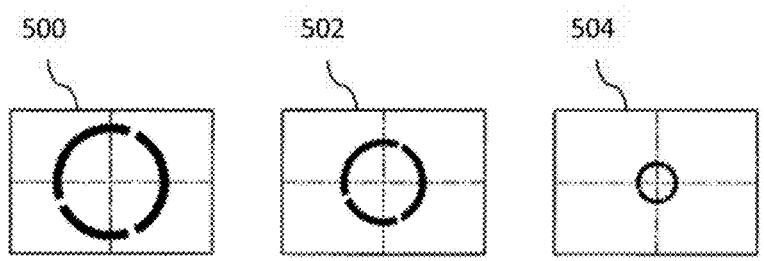

TOPOGRAPHICAL IMAGING USING COMBINED SENSING INPUTS

BACKGROUND

The present disclosure relates generally to topographical imaging and, more specifically, to topographical imaging using optical coherence tomography (OCT) and an image sensor.

Scheimpflug corneal topography is an imaging technique. This imaging technique is typically used in a medical setting for imaging corneal shape. A camera is positioned to observe a profile of the corneal shape from one perspective. The camera is rotated about the cornea until the camera observes the profile from approximately the full 360° view. Due to the mechanical movement of the camera, Scheimpflug corneal topography can suffer from drawbacks including, for instance, distortion as a result of eye movement.

Optical coherence tomography (OCT) is another imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

SUMMARY

The present technology provides improved topographical imaging.

In one implementation of the present technology, an optical system is disclosed. The optical system includes an optical coherence tomography (OCT) system arranged to project a beam scan towards a target and configured to generate data corresponding to the beam scan. The optical system also includes an image sensor arranged to capture an image of a trace of the beam scan on a surface of the target. The optical system also includes a computing system including a processing circuit including a processor and memory. The memory is structured to store instructions that, when executed by the processor, cause the processor to process the image captured by the image sensor to determine one or more characteristics of the target based, at least in part, on the trace of the beam scan.

In another implementation of the present disclosure, an optical system is disclosed. The optical system includes an optical coherence tomography (OCT) system arranged to project a beam scan towards a target and configured to generate data corresponding to the beam scan. The optical system also includes an image sensor arranged to capture an image of a trace of the beam scan on a surface of the target. The optical system also includes a computing system including a processing circuit including a processor and memory. The memory is structured to store instructions that, when executed by the processor, cause the processor to process beam scan data received from the OCT system to identify a coordinate map for the beam scan data including a first set of coordinates of the surface for the target. The memory is also structured to store instructions that, when executed by the processor, cause the processor to process the image captured by the image sensor to identify a second set of coordinates for the surface of the target. The memory is also structured to store instructions that, when executed by the processor, cause the processor to modify the relative coordinate map for the beam scan data based on the second set of coordinates.

In another implementation of the present technology, a method of topographical imaging is disclosed. The method includes receiving beam scan data from an optical coherence tomography (OCT) system arranged to project a beam scan towards a target and configured to generate the beam scan data. The method also includes processing the beam scan data to identify a coordinate map of the target including a first set of coordinates for a surface of the target. The method also includes receiving an image of a trace of the beam scan on the surface of the target from an image sensor. The method also includes processing the image to identify a second set of coordinates for the surface of the target. The method also includes modifying the coordinate map according to the second set of coordinates.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4 depicts an example of an image captured by the imaging system of FIG. 3 in accordance with an illustrative embodiment.

FIG. 5 depicts an example of a target of the optical system of FIG. 3 and several example images in accordance with an illustrative embodiment.

DETAILED DESCRIPTION

Figure 1:
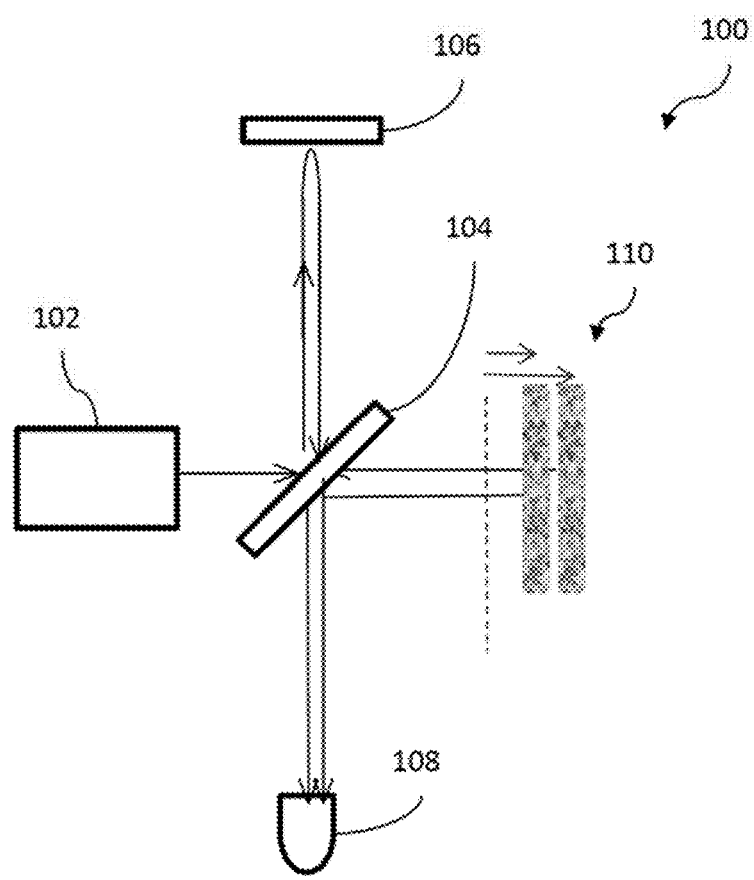
FIG. 1 depicts an OCT system in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein are systems and methods for topographical imaging. The aspects described herein leverage the benefits of OCT systems and the accuracy of video-Placido-keratometry.

As will be discussed in further detail below, an OCT system is arranged to capture a three-dimensional (3D) OCT scan of a target. The OCT system generally projects a beam scan towards the target, and the OCT system generates data corresponding to the beam scan. Additionally, an image sensor is arranged to capture an image of a trace of the beam scan on a surface of the target. Using the image of the trace, various characteristics of the target can be determined.

Referring now to FIG. 1, a schematic diagram of an OCT system 100 is shown, according to one example embodiment. The OCT system 100 includes a light source 102, a beam splitter 104, a reference mirror 106, and a detector 108. Additionally, the OCT system 100 is shown to include a target 110. As used herein, target refers to the sample being imaged by the OCT system. Generally speaking, the light source 102 projects light to the beam splitter 104. The beam splitter 104 splits the light from the light source 102 onto the reference mirror 106 and onto the target 110. Based on light reflected from the reference mirror 106 and the target 110 (e.g., based on an interferogram generated form the reflected light), a depth can be determined at a point on the target 110. Following manipulation of the light across the target 110, a 3D OCT scan can be formed. As will be discussed in further detail below, the light from the light source 102 may have a particular wavelength that is observable by an image sensor. In so doing, various characteristics of the target 110 may be determined. For instance, coordinates for a surface of the target 110 may be determined, which may be used for modifying a coordinate map corresponding to the 3D OCT scan. Additionally or alternatively, a profile of one surface of the target 110 may be determined and used for constructing a 3D model of a portion of the 3D model, and depths as determined via the 3D OCT scan can be used for providing anterior or posterior surfaces within the 3D model. Additionally or alternatively, a size of a projected pattern on the target can be compared to a calibrated pattern for purposes of performing auto-refractometry.

In one or more implementations, the OCT system 100 may be a time-domain OCT system. In these implementations, the light source 102 may be a low coherence light source. Light from the light source 102 may be directed to the target 110 through an interferometer. The beam splitter 104 splits the light from the light source 102 into a sample arm and a reference arm. The sample arm is projected onto the target 110, and the reference arm is projected onto the reference mirror 106. The sample arm penetrates the target 110, and back-scattered light from the sample arm is detected by the interferometer. Additionally, the reference arm (which is reflected off the reference mirror 106) is detected by the interferometer. The combination of the reflected light from the reference mirror 106 and the reflected light from the target 110 is used to form an interference pattern (e.g., a difference in optical distance traveled by reflected photons from both the reference arm and the sample arm). Based on the interference, an amplitude and position of reflection (e.g., a depth) from inside the target 110 can be determined. Additionally, the reference mirror 106 may be moved, which thereby changes the optical path length of the reference path. The amplitude and position of reflection may be recorded along the depth direction, which forms an OCT signal (e.g., an A-scan). In this regard, the OCT signal is a two-dimensional (2D) scan of the target 110 including depths to various surfaces. The 2D scan of the target 110 may have coordinates of various surfaces of the target 110 associated therewith. To form a 3D scan, the light projected onto the target 110 is geometrically moved about the sample 110. The 2D scans following movement collectively form a 3D OCT scan (e.g., a B-scan). Accordingly, the 3D scan may have a plurality of coordinates associated with the various surfaces and layers of the target 110, each of which corresponds to individual 2D scans.

In one or more implementations, the OCT system 100 may be a swept-source OCT system. In these implementations, the light source 102 may be a high coherence light source. Light from the light source 102 may be directed to the target 110 through an interferometer. The beam splitter 104 splits the light from the light source 102 into a sample arm and a reference arm. The sample arm is projected onto the target 110, and the reference arm is projected onto the reference mirror 106. The sample arm penetrates the target 110, and back-scattered light from the sample arm is detected by the interferometer. Additionally, the reference arm (which is reflected off the reference mirror 106) is detected by the interferometer. The combination of the reflected light from the reference mirror 106 and the reflected light from the target 110 is used to form an interference pattern (e.g., a difference in optical distance traveled by reflected photons from both the reference arm and the sample arm). Based on the interference, an amplitude and position of reflection (e.g., a depth) from inside the target 110 can be determined. In the swept-source OCT system, rather than the reference mirror 106 being moved, the light from the light source is tuned over a wavelength range. The detector 108 receives a temporal signal having different frequency components. A Fourier transform is operated on the temporal signal to form the OCT signal (e.g., the 2D scan), with the frequency component corresponding to the depth position of various surfaces and the amplitude corresponding to reflectivity. Similar to the time-domain OCT, the 2D scan of the target 110 may have coordinates for the various surfaces associated therewith. Additionally, to form a 3D scan, the light projected onto the target 110 is geometrically moved about the sample 110. The 2D scans following movement collectively form a 3D OCT scan (e.g., a B-scan). Accordingly, the 3D scan may have a plurality of coordinates associated with the various surfaces and layers of the target 110, each of which corresponds to individual 2D scans.

Figure 2:
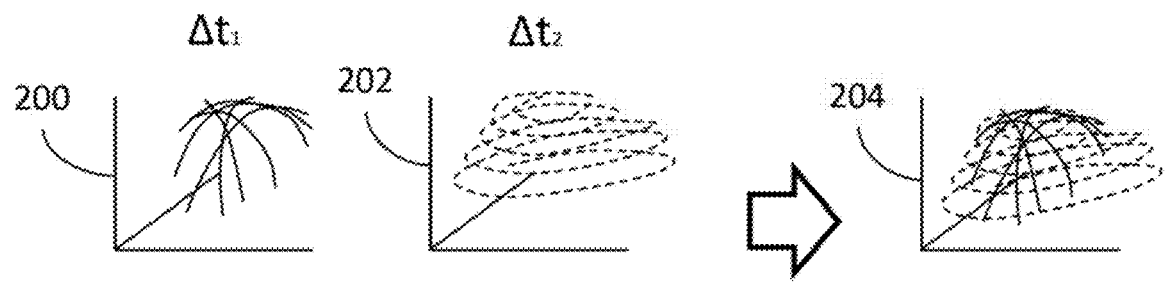
FIG. 2 depicts example scans of an OCT system in accordance with an illustrative embodiment.

Referring now to FIG. 1 and FIG. 2, in some embodiments, the OCT system 100 may generate two or more B-scans. For instance, in the example shown in FIG. 2, the OCT system 100 may generate a first B-scan 200 and a second B-scan 202. The first B-scan 200 may be captured at a first rate $\Delta t_1$ and the second B-scan 202 may be captured at a second rate $\Delta t_2$. In some implementations, the first B-scan 200 may be taken at a faster rate than the second B-scan 202 (e.g., $\Delta t_1 > \Delta t_2$. In these implementations, the first B-scan 200 may be used to establish global coordinates for the target 110. The first B-scan 200, in being taken at a faster rate, may not include as many detailed data samples (e.g., 2D scans) as the second B-scan 200. However, the first B-scan 200, in being taken at a faster rate, may have more accurate global coordinates for the target 110. This is of particular relevance where the target 110 may move (as one example, where the target 110 is an eye or a portion thereof). The second B-scan 202, in being taken at a slower rate, may include more detailed data samples (e.g., more A-scans).

However, the B-scan 202 may be distorted due to, for instance, movement of the target 110.

In some embodiments, the first B-scan 200 and the second B-scan 202 may be merged to form B-scan 204. In one implementation, global coordinates from the first B-scan 200 may be used to adjust global coordinates and distortions of the second B-scan 202. In so doing, the benefits of both the first and second B-scans 200, 202 may be leveraged to form B-scan 204.

In some embodiments, the first B-scan 200 and/or second B-scan 202 may be in a pattern and/or have a particular size. For instance, the first B-scan 200 and/or second B-scan 202 may have a pattern similar to a pattern from a Placido cone (e.g., concentric circles). As another example, the first B-scan 200 and/or second B-scan 202 may have a spiral pattern, a raster pattern, or a radial pattern, to name a few possibilities.

In some instances, the first B-scan 200 and/or second B-scan 202 may scan a predetermined area of the target 110. As one example, the predetermined area may be a circle defined by a predetermined diameter or radius. This example is of particular relevance where the target 110 is a cornea. For instance, the predetermined radius may be 2.00 mm, 2.25 mm, 2.50 mm, 2.75 mm, 3.00 mm, 3.25 mm, to name a few possibilities. In instances such as these, the predetermined radius may correspond to an average corneal size or keratometrical zone size. Accordingly, the B-scans 200, 202 may have increased accuracy by leveraging more data samples across a smaller area.

In some embodiments, the OCT system 100 may process and/or refine B-scan 200 and/or B-scan 202. For instance, the OCT system 100 may apply one or more filters to the data from B-scan 200 and/or B-scan 202. The OCT system 100 may filter the data to remove outliers. As one example, the OCT system 100 may filter the data according to average curvature for the target 110. For instance, where the target 110 is a cornea, the OCT system 100 may filter the data based on average corneal curvature. The filter may be a range of average corneal curvatures (for instance, a 5.00-10.00 mm radius curvature, to name one example). The OCT system 100 may remove data according to the filter (e.g., data outside the range).

In some embodiments, the light projected from the light source 102 onto the target 110 may be telecentric. Accordingly, in some embodiments, the light projected onto the target 110 may be perpendicular to one or more surface within the OCT system 100. In some instances, the light may be perpendicular to a lens (e.g., lens 334 of FIG. 3). In some embodiments, such as those described with reference to FIG. 5, the light projected onto the target 110 may be non-telecentric.

While these examples are provided, a number of different and/or modified OCT systems and scan patterns may be implemented, substituted, and/or incorporated into the disclosed systems and methods. Accordingly, the present disclosure is not limited to a particular OCT system. While the light source 102 indirectly projects light onto the target 110, hereinafter any reference to light projected onto the target 110 is generally referring to configurations and variations of light projections in OCT systems 100 for purposes of readability.

In one or more embodiments, the light source 102 may project light having a specific wavelength. For instance, the light source 102 may project light in the infrared spectrum, to name one example.

Figure 3:
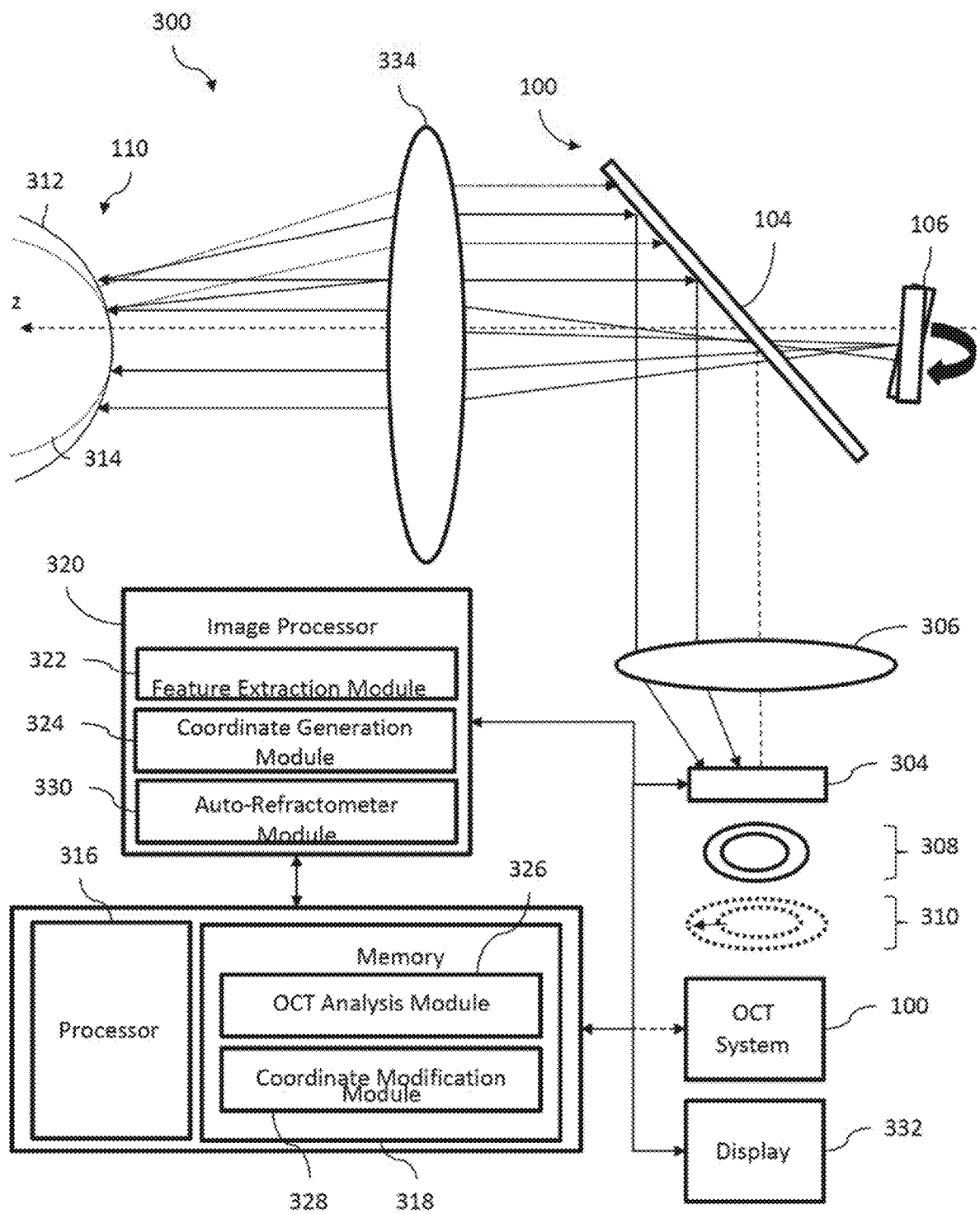
FIG. 3 depicts an optical system including the OCT system of FIG. 1 and an imaging system in accordance with an illustrative embodiment.

Referring to FIG. 3, an optical system 300 is shown in accordance with an illustrative embodiment. The optical system 300 includes an OCT system 100 similar to that described above with reference to FIG. 1. Additionally, the optical system 300 includes an imaging system 302. The imaging system 302 is shown to include an image sensor 304 and an imaging lens 306. In some implementations, the image sensor 304 may be a complementary metal-oxide semiconductor (CMOS) image sensor. The image sensor 304 may be arranged to detect light from beam splitter 104. In this embodiment, beam splitter 104 may be or include, for instance, a half mirror. In this regard, the image sensor 304 may be configured to capture an image of target 110 through the reflection off the half mirror. In particular, the image sensor 304 may capture an image of a surface of target 110 (for instance, an outer surface of the target 110).

As stated above, the light from light source 102 of the OCT system 100 may project light having a wavelength. In some embodiments, the image sensor 304 may be sensitive to light in a spectrum of wavelengths including, at least, the wavelength of light projected by the light source 102. Accordingly, the image captured by image sensor 304 may include light projected by the light source 102 onto the target 110. In arrangements where the first and/or second B-scan 200, 202 have a pattern, the pattern may be reflected in the image of the target 110. For instance, where the pattern includes concentric circles, the image of the target 110 may include features that correspond to the concentric circles.

As stated above, the pattern from the light source 102 may be projected at a rate $\Delta t$. Additionally, the image sensor 304 may have an exposure rate. In some implementations, the exposure rate for may be less than rate $\Delta t$. In implementations such as these, the image sensor 304 may acquire a series of images. The series of images may be superimposed upon one another to form an image that captures an image of the target 110 that spans, at least, $\Delta t$. In other implementations, the rate $\Delta t$ may be less than or equal to the exposure rate for the image sensor 304. In implementations such as these, the image sensor 304 may acquire an image of the target for a duration greater than or equal to the rate $\Delta t$.

Referring briefly to FIG. 4, an example image 400 of the target 110 is shown. In this example, target 110 is a cornea of an eye. The image 400 includes a trace 402 of the B-scan (e.g., B-scan 200 and/or B-scan 202). Trace, as used herein, is a visual effect of a B-scan on a surface of a target. As shown, the trace 402 includes two concentric circles which are reflected off the cornea of the eye. In some implementations, the pattern may include additional concentric circles. In each of these examples, the image sensor 304 acquires an image 400 that includes, at least, the trace 402 of the B-scan on the target 110. The image 400 may be a superimposed image compiled from a series of images of the target 110. Additionally or alternatively, the image 400 may be a single image of the target 110.

Referring now to FIG. 3 and FIG. 4, the light source 102 of the OCT system 100 may project concentric circles towards the target 110. The concentric circles may be projected during the first B-scan 200, the second B-scan 202, and/or other B-scans. Upon interacting with the target 110, the trace 402 may have a different shape. For instance, as a surface of the target 110 flattens, the concentric circles within the trace 402 may be less spaced apart. Additionally, as a surface of the target 110 is sloped, the concentric circles within the trace 402 become spaced apart. This can be best seen in the progression between concentric circles 308 and concentric circles 310 and the corresponding surface profiles for their respective target 312, 314. As shown, target 314 has a surface profile that is more sloped than target 312. Accordingly, concentric circles 310 (which are those observed on the surface of target 314) are more spaced apart than concentric circles 308 (which are those observed on the surface of target 312). As additional concentric circles are added to the trace 402, a surface profile for the target 110 may be identified based on the width between concentric circles.

Referring back to FIG. 3, in some implementations, the surface profile for the target 110 may be used to determine one or more coordinates for the surface of the target 110.

In some embodiments, the optical system 300 can include an optical analysis processing circuit. The optical analysis processing circuit can include a processor 316 and memory 318. The processor 316 may include any component or group of components that are configured to execute, implement, and/or perform any of the processes or functions described herein or any form of instructions to carry out such processes or cause such processes to be performed. In one or more arrangements, the processor 316 can be a main processor of the optical system 300. Examples of suitable processors include microprocessors, microcontrollers, DSP processors, and other circuitry that can execute software. Further examples of suitable processors include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller. The processor 316 can include at least one hardware circuit (e.g., an integrated circuit) configured to carry out instructions contained in program code. In arrangements in which there is a plurality of processors, such processors can work independently from each other or one or more processors can work in combination with each other.

The memory 318 can be structured for storing one or more types of data. The memory 318 store can include volatile and/or non-volatile memory. Examples of suitable memory 318 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The memory 318 can be a component of the processor 316, or the memory 318 can be operatively connected to the processor 316 for use thereby. In some arrangements, the memory 318 can be located remotely and accessible by the processor 316, such as via a suitable communications device.

In some embodiments, the optical analysis processing circuit can include an image processor 320. The image processor 320 can be or include various devices, components, and/or software configured to identify features within an image. For instance, the image processor 320 can include a feature extraction module 322, a coordinate generation module 324, and an auto-refractometer module 330. Each of these modules 322, 324, 330 can be or include a set of instructions stored on memory (e.g., memory 318, for instance) that, when executed by the image processor 320, cause the image processor 320 to execute various functions. In some implementations, the image processor 320 and memory may be stored locally (e.g., within the optical analysis processing circuit). Additionally or alternatively, the image processor 320 and memory may be stored remotely. Additionally or alternatively, the image processor 320 may be stored locally (e.g., within the optical analysis processing circuit) and the memory may be stored remotely (and vice versa).

In one or more embodiments, the feature extraction module 322 can include instructions that, when executed by the image processor 320, cause the image processor 320 to extract features that are represented in the image. The feature extraction module 322 can include instructions for identifying edges of various features contained in the image, instructions for segmentation and block matching, and/or other techniques for extracting features within an image. The image processor 320 may receive an image (e.g., image 400, for instance) captured by the image sensor 304. The image processor 320 can process the image to extract features within the image received from the image sensor 304. Continuing the example, the image processor 320 can process image 400 to extract concentric circles contained in the image 400.

Referring now to FIG. 3 and FIG. 5, another example of a target 110 of the optical system 300 is shown. Additionally, as shown in FIG. 5, several example images 500, 502, 504 are provided. In the example of FIG. 5, the target 110 is an eye. In this example, light from light source 102 is projected to have a pattern B. The pattern B in this example includes circular segments. Additionally, the pattern B has a particular orientation defined by axes X and Y. The pattern B is projected onto the eye at a first location P1 (e.g., at the cornea). As can be seen, light projected from light source may be non-telecentric. Accordingly, incoming light from light source 102 is, at least partially, angled with respect to a lens in the optical system 300 (e.g., lens 334).

As stated above, image sensor 304 may capture an image of the target 110. The image may include light from light source 102 that is reflected off target 110. Continuing the example of FIG. 5, the image sensor 304 may capture an image of the eye including the pattern B at location P1. Additionally, light may penetrate the eye and reflect off the back of the eye at another location P2. In some examples, depending on the shape, size, and/or other characteristics of the eye, the pattern B may change when observed at location P2. For instance, the pattern B may be inverted at P2, the pattern B may have a different size at location P2, etc. The image captured by image sensor 304 may include the pattern B at location P2.

In one or more embodiments, the feature extraction module 322 can include instructions for identifying the size, location, and/or orientation of pattern B at location P2. For instance, the feature extraction module 322 can include instructions to identify the location of pattern B at location P1 using techniques similar to those described above with respect to identifying the concentric circles. The feature extraction module 322 can include instructions to identify the pattern B at location P2 based on its expected location with respect to location P1. The feature extraction module 322 can include instructions to identify the location of pattern B at location P2. Once pattern B is located at location P2, various features of pattern B can be extracted. For instance, the feature extraction module 322 can include instructions for determining a size of the pattern B. The feature extraction module 322 can include instructions for determining an orientation of the pattern B (for instance, with respect to axes X and Y). The feature extraction module 322 can include instructions for determining a location of a portion (e.g., a center, a particular space between two segments, etc.) of pattern B at location P2 with respect to a location of a portion of pattern B at location P1 (e.g., the center, the particular space between the same two segments, etc.).

Referring now to FIG. 3, in one or more embodiments, the image processor 320 can include a coordinate generation module 324. The coordinate generation module 324 can include instructions that, when executed by the image processor 320, cause the image processor 320 to generate coordinates based on the extracted features of the image. The coordinate generation module 324 can include instructions for comparing a width between concentric circles to stored information that corresponds to a slope. The coordinate generation module 324 can include instructions for identifying coordinates based on the slope. For instance, the coordinate generation module 324 can include instructions for identifying (x,y,z) coordinates based on the slope at various locations along the surface of the target 110. Such information may be used for modifying, for instance, coordinates contained in B-scan 200, 202, and/or 204.

In some embodiments, the memory 318 may store an OCT analysis module 326. The OCT analysis module 326 can include instructions that, when executed by processor 316, cause the processor 316 to process data received from the OCT system 100. For instance, the OCT analysis module 326 can include instructions to identify various surfaces and/or thicknesses associated with various surfaces in a B-scan (e.g., B-scan 200, 202, 204). The OCT analysis module 326 can include instructions to construct a coordinate map (e.g., similar to the map shown in B-scan 200, 202, and/or 204) for the B-scan. Each point in the coordinate map can have coordinates associated therewith. Accordingly, the coordinate map can include the coordinates received from the OCT system 100 for surfaces mapped on and within the target 110.

In some embodiments, the memory 318 may store a coordinate modification module 328. The coordinate modification module 328 can include instructions, that, when executed by processor 316, cause the processor 316 to modify and/or replace coordinates within the coordinate map identified via OCT analysis module 326. For instance, the coordinate modification module 328 can include instructions for modifying and/or replacing coordinates within the coordinate map with coordinates identified via the coordinate generation module 324 of the image processor 320. As one example, the coordinate modification module 328 can include instructions for replacing coordinates of the coordinate map with coordinates for the surface of the target 110 identified within the image processed via image processor 320. The coordinate modification module 328 can include instructions for modifying the remaining coordinates for other surfaces contained in the coordinate map according to the coordinates within the image processed via the image processor 320. In this and other examples, the disclosed system leverages the accuracy of the coordinates identified within the image and the accuracy of the measurements and resulting coordinates obtained via the OCT system 100.

In some embodiments, the coordinate modification module 328 can include instructions that, when executed by the processor 316, cause the processor 316 to calculate one or more properties of the target 110 based on the coordinate map. For instance, the coordinate modification module 328 can include instructions to calculate a curvature of one or more surfaces of the target based on data from the coordinate map. In some examples, the coordinate modification module 328 can include instructions to calculate the curvature of one or more surfaces using at least three points for a surface of the target 110 as represented within the coordinate map. In examples where the target 110 is an eye, the curvature may be the anterior and/or posterior corneal curvature. Accordingly, where the coordinate map is modified according to the coordinates obtained via the coordinate generation module 324, any of the anterior or posterior corneal curvature may be calculated by identifying the curvature according to coordinates obtained via the coordinate generation module 324, and adding (or subtracting) depth for the other corneal curvature. In this example, the corneal curvature (e.g., anterior and posterior) may be calculated more accurately than traditional calculations by leveraging accuracy from the image obtained via image sensor 304 and accuracy from the OCT system 100.

Referring back to FIG. 3 and FIG. 5, in one or more embodiments, the image processor 320 may include an auto-refractometer module 330. The auto-refractometer module 330 can include instructions that, when executed by the image processor 320, cause the image processor 320 to compare the features extracted from an image (e.g., the image of pattern B at location P2) to one or more calibrated images. Continuing the example of FIG. 5, a size of the pattern B at location P2 can be compared to a calibrated size (e.g., a size associated with an eye having 20/20 vision, for instance). As one example, image 502 may be the calibrated size of pattern B which is to be expected (referred to hereinafter as "the calibrated image 502"). The auto-refractometer module 330 can include instructions for determining whether the pattern B at location P2 is has a size that is greater than or less than pattern B within the calibrated image 502. Where the pattern B at location P2 has a size that is greater than pattern B within the calibrated image 502, the auto-refractometer module 330 can include instructions for generating data indicating a near-sighted condition (e.g., myopia) for the eye. Alternatively, where the pattern B at location P2 has a size that is less than pattern B within the calibrated image 502, the auto-refractometer module 330 can include instructions for generating data indicating a far-sighted condition (e.g., hyperopia) for the eye. As another example, the auto-refractometer module 330 can include instructions to compare an orientation of the pattern B within the image captured by the image sensor 304 to the pattern B within the calibrated image 502. As one example, the auto-refractometer module 330 can include instructions to generate data indicating near-sighted condition for the eye where the pattern B within the image captured by the image sensor 304 is inverted with respect to the pattern B within the calibrated image 502.

In some embodiments, the auto-refractometer module 330 can include instructions to determine a refractive power associated with each condition based on the comparison of patterns B at location P2 within the image captured by image sensor 304 and the calibrated image 502. For instance, the auto-refractometer module 330 can include instructions to determine a refractive power based on the degree of which the sizes are different for patterns B at location P2 within the image and the calibrated image 502.

In some embodiments, the auto-refractometer module 330 can include instructions to identify astigmatism of the eye based on a comparison of the image captured by image sensor 304 and the calibrated image 502. For instance, the auto-refractometer module 330 can include instructions to compare the location of the pattern B at location P2 with respect to quadrants defined by axes X and Y and the calibrated image 502. Where the location of pattern B at location P2 within the image captured by image sensor 304 is different from the location of pattern B within the calibrated image 502, the auto-refractometer module 330 can include instructions to generate data indicating astigmatism of eye.

In some embodiments, the optical system 300 may include a display 332. The display 332 can be any device and/or component configured to display an image to a user.

For instance, the display 332 can be a cathode ray tube (CRT) display, a light-emitting diode (LED) display, an liquid crystal display (LCD), a plasma display panel (PDP), to name a few possibilities. The display 332 may be operatively connected to the processor 316 and controlled thereby. The processor 316 may control the display 332 to display an image of the target 110. The image may be or include the coordinate map generated and/or modified via the coordinate modification module 328. Additionally or alternatively, the image may be or include the beam scan data. Additionally or alternatively, the image may be or include the image captured by the image sensor 304. In some arrangements, the processor 316 can control the display 332 to display additional data. For instance, the processor 316 can control the display 332 to display data corresponding to the various conditions indicated via the auto-refractometer module 330. As another example, the processor 316 can control the display 332 to display other calculated characteristics of the target (e.g., anterior and/or posterior curvature, for example).

Figure 6:
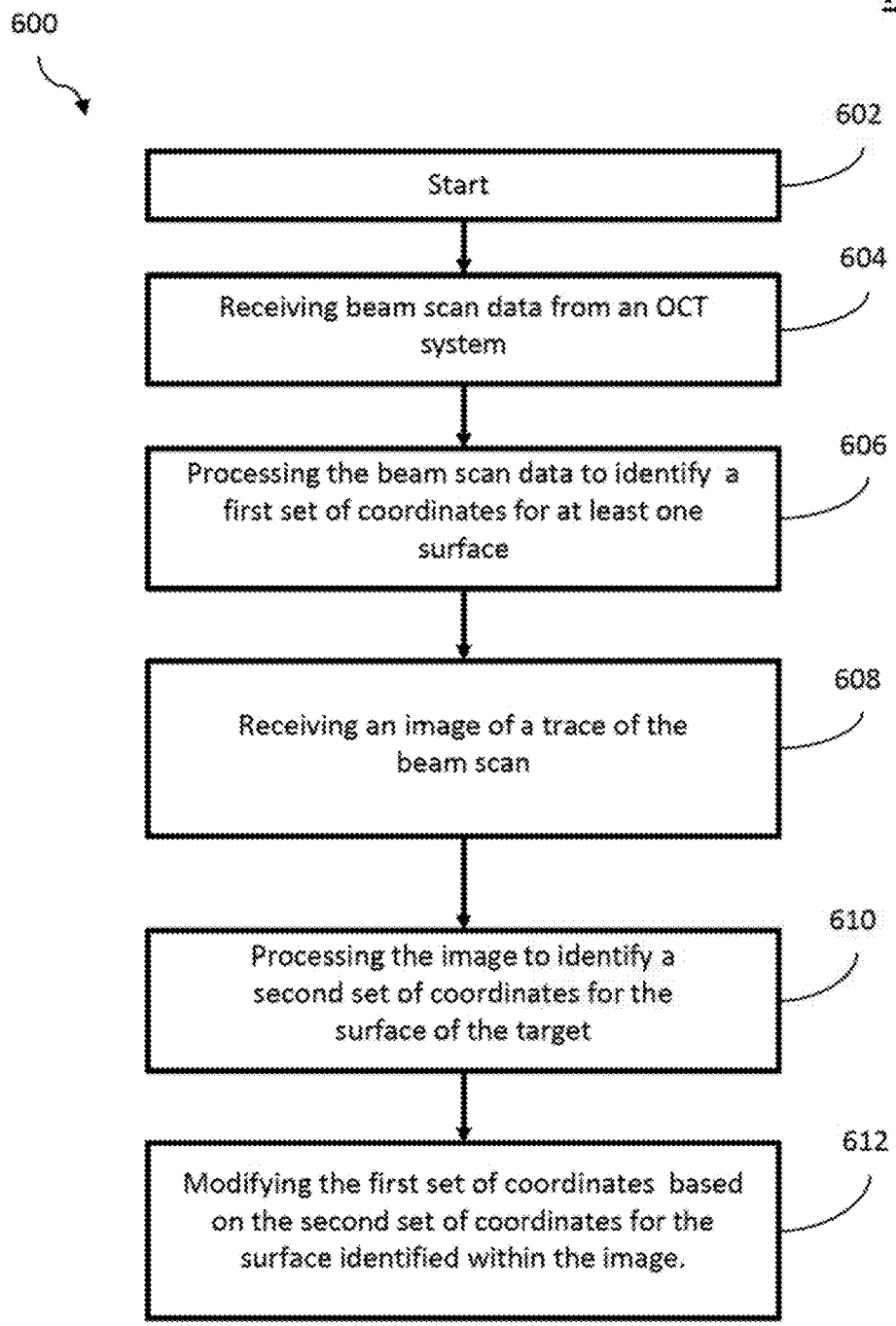
FIG. 6 depicts a flow chart showing an example method of topographical imaging a target in accordance with an illustrative embodiment.

Now that various aspects of the disclosed systems and components have been described, a method of topographical imaging a target will be described with reference to FIG. 6. The flow chart shown in FIG. 6 provides only one example of topographical imaging a target. Accordingly, the following disclosure should not be limited to each and every function block shown in FIG. 6. To the contrary, the method does not require each and every function block shown in FIG. 6. In some examples, the method may include additional function blocks. Further, the method does not need to be performed in the same chronological order shown in FIG. 6.

Referring now to FIG. 6, a flow chart is shown to depict an example method 600 of topographical imaging of a target 110 in accordance with an illustrative embodiment.

The method 600 can include operation 602. At operation 602, the method 600 may begin. The method 600 may begin when an initialization signal (e.g., from a user) is received by the various components/systems described herein. The method 600 can proceed to operation 604.

At operation 604, the method 600 can include receiving beam scan data from OCT system 100. The beam scan may be of a target 110. The beam scan data can include one or more B-scans 200, 202. The B-scans 200 may have a pattern (e.g., pattern B of FIG. 5, pattern shown in trace 402 of FIG. 4, etc.). The beam scan data may include coordinates (e.g., local coordinates) for A-scans that make up the respective B-scan 200, 202. Collectively, the B-scan 200, 202 can include one or more global coordinates, as described above. In some implementations, the beam scan data may be received by processor 316. The method 600 can proceed to operation 606.

At operation 606, the method 600 can include processing the beam scan data from the OCT system 100 to identify a first set of coordinates. In some implementations, the first set of coordinates may be the global coordinates and/or the local coordinates contained in B-scan 200, 202. In one or more arrangements, the processor 316 can process the beam scan data using instructions from the OCT analysis module 326. The processor 316 can generate a coordinate map based on the beam scan data received from the OCT system 100. The method 600 can proceed to operation 608.

At operation 608, the method 600 can include receiving an image of a trace of the beam scan. The image may be received from image sensor 304. The image may be of the target 110. The trace of the beam scan may be on a surface of the target 110. In some examples, the image may be similar to images 500, 502, 504. In other examples, the image may be similar to image 400. The method 600 can proceed to operation 610.

At operation 610, the method 600 can include processing the image to identify another set of coordinates. In some implementations, the coordinates may be identified by image processor 320 using instructions from the coordinate generation module 324. The coordinates identified via coordinate generation module 324 may be of a surface of target 110. The method 600 can proceed to operation 612.

At operation 612, the method 600 can include modifying the first set of coordinates identified at operation 606 based on the coordinates identified at operation 610. As stated above, the coordinates identified at operation 606 for the surface of target 110 can be replaced and/or modified based on the coordinates identified via coordinate generation module 324. Additionally, the remaining coordinates identified at operation 606 can be modified in accordance with to the modified coordinates. Accordingly, the coordinates for target 110 can include some coordinates identified within the image received at operation 608 and others identified at operation 606. In so doing, the coordinate map for target 110 leverage the accuracy of the coordinates identified in the image received at operation 610 with other measurements and coordinates associated therewith identified at operation 606. These coordinates (for instance, the coordinate map) can be displayed to a user via display 332.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions.

Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary.

It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety.

Definitions that are contained in text incorporated by reference are excluded to the extent that they contradict definitions in this disclosure.

Other embodiments are set forth in the following claims.

What is claimed is:

1. An optical system comprising:
   an optical coherence tomography (OCT) system arranged to project a beam scan towards a target and configured to generate data corresponding to the beam scan, wherein the OCT system projects the beam scan along a path to form a pattern on a first surface of the target;
   an image sensor arranged to capture an image of a trace of the beam scan on the first surface of the target, wherein the image of the trace comprises a visual effect corresponding to the pattern on the first surface of the target in the image; and
   a computing system including an optical analysis processing circuit, the optical analysis processing circuit including a processor and memory, the memory being structured to store instructions that, when executed by the processor, cause the processor to:
      generate, using the data generated by the OCT system corresponding to the beam scan, a coordinate map of the surface of the target comprising coordinates corresponding to the first surface of the target and a second surface of the target; and
      modify, using the image of the trace of the beam scan on the first surface of the target, at least a portion of the coordinates of the coordinate map corresponding to the first surface or the second surface of the target based on a relationship of the visual effect shown in the image and the pattern corresponding to the path of the beam scan, wherein the coordinates are first coordinates, and wherein modifying, using the image of the trace of the beam scan on the first surface of the target, at least the portion of the coordinates of the coordinate map corresponding to the first surface or the second surface of the target based on the relationship of the visual effect shown in the image and the pattern corresponding to the path of the beam scan comprises:
         generating a surface profile for the first surface of the target using the visual effect shown in the image;
         determining second coordinates for the surface profile of the first surface based on a slope corresponding to a relationship between the visual effect shown in the image and the pattern corresponding to the path; and
         replacing, in the coordinate map, one or more of the first coordinates for the first surface with one or more of the second coordinates determined for the surface profile of the first surface.

2. The optical system of claim 1, wherein the beam scan has an electromagnetic frequency in the infrared spectrum, and wherein the image sensor is sensitive to electromagnetic frequencies in the infrared spectrum.

3. The optical system of claim 1, wherein the beam scan projected by the OCT system has at least one geometric property, and wherein the memory is further configured to store instructions that, when executed by the processor, cause the processor to determine a refractive power being determined based on a geometric property of the beam scan as represented in the image with respect to a predetermined geometric property.

4. The optical system of claim 3, wherein the geometric property of the beam scan as represented in the image is any of a size of the beam scan represented in the image or an orientation of the beam scan represented in the image.

5. The optical system of claim 3, wherein the beam scan is a non-telecentric beam scan.

6. The optical system of claim 1, wherein the image sensor has an exposure rate that is less than a scan rate for the beam scan.

7. The optical system of claim 6, wherein the image sensor is arranged to capture a plurality of images within one scan rate for the OCT system.

8. The optical system of claim 7, wherein the image of the trace of the beam scan is a set of the plurality of images that collectively capture the trace of the beam scan on the surface of the target.

9. The optical system of claim 1, wherein the instructions to modify the portion of the coordinate map comprise instructions to:
   modify the portion of the coordinate map corresponding to the first surface to replace coordinates for the first surface with the coordinates obtained for the first surface using the trace of the beam scan within the image from the image sensor; and
   modify coordinates corresponding to the OCT system according to the replaced coordinates of the coordinate map for the first surface.

10. An optical system comprising:
    an optical coherence tomography (OCT) system arranged to project a beam scan towards a target and configured to generate data corresponding to the beam scan, wherein the OCT system projects the beam scan along a path to form a pattern on a first surface of the target;
    an image sensor arranged to capture an image of a trace of the beam scan on the first surface of the target, wherein the image of the trace comprises a visual effect corresponding to the pattern on the first surface of the target in the image; and
    a computing system including a processing circuit, the processing circuit including a processor and memory, the memory being structured to store instructions that, when executed by the processor, cause the processor to:

process beam scan data received from the OCT system to generate a coordinate map for the first surface of the target, the coordinate map corresponding to the beam scan data and including a first set of coordinates of the first surface for the target;

process the image captured by the image sensor to identify a second set of coordinates for the first surface of the target, wherein the second set of coordinates are identified based on a relationship of the visual effect shown in the image and the pattern corresponding to the path of the beam scan; and modify a portion of the first coordinates of the coordinate map corresponding to the first surface of the target using the second set of coordinates identified using the image of the trace of the beam scan, wherein modifying the portion of the coordinates of the first coordinates of the coordinate map corresponding to the first surface of the target comprises:

generating a surface profile for the first surface of the target using the visual effect shown in the image;

determining second coordinates for the surface profile of the first surface based on a slope corresponding to a relationship between the visual effect shown in the image and the pattern corresponding to the path; and replacing, in the coordinate map, one or more of the first coordinates for the first surface with one or more of the second coordinates determined for the surface profile of the first surface.

11. The optical system of claim 10, wherein the memory further stores instructions that, when executed by the processor, cause the processor to:

replace the first set of coordinates with the second set of coordinates.

12. The optical system of claim 11, wherein the memory further stores instructions that, when executed by the processor, cause the processor to:

modify other coordinates within the coordinate map corresponding to the beam scan data according to the second set of coordinates.

13. The optical system of claim 11, wherein the memory further stores instructions that, when executed by the processor, cause the processor to:

calculate a curvature of another surface of the target based on a thickness associated with at least three coordinates of the coordinate map.

14. The optical system of claim 11, wherein the first surface comprises at least one of an anterior corneal surface or a posterior corneal surface.

15. The optical system of claim 14, wherein the beam scan is of a fixed area of the target, the fixed area having proportions corresponding to an average corneal size or keratometrical zone size.

16. A method of topographical imaging, the method comprising:

receiving, by a computing system from an optical coherence tomography (OCT) system arranged to project a beam scan towards a target, beam scan data generated by the OCT system and corresponding to a first surface of the target, wherein the OCT system projects the beam scan along a path to form a pattern on a first surface of the target;

processing the beam scan data to generate a coordinate map of the target including a first set of coordinates for the first surface of the target;

receiving an image of a trace of the beam scan on the first surface of the target from an image sensor, wherein the image of the trace comprises a visual effect corresponding to the pattern on the first surface of the target in the image;

processing the image to identify a second set of coordinates for the surface of the target, wherein the second set of coordinates are identified based on a relationship of the visual effect shown in the image and the pattern corresponding to the path of the beam scan; and modifying a portion of the first set of coordinates of the coordinate map corresponding to the first surface of the target using the second set of coordinates identified using the image of the trace of the beam scan, wherein modifying the portion of the coordinates of the first coordinates of the coordinate map corresponding to the first surface of the target comprises:

generating a surface profile for the first surface of the target using the visual effect shown in the image;

determining second coordinates for the surface profile of the first surface based on a slope corresponding to a relationship between the visual effect shown in the image and the pattern corresponding to the path; and replacing, in the coordinate map, one or more of the first coordinates for the first surface with one or more of the second coordinates determined for the surface profile of the first surface.

17. The method of claim 15, wherein processing the beam scan further comprises:

comparing the beam scan data to a preset range; and filtering data outside of the preset range.

18. The method of claim 15, wherein receiving the beam scan data further comprises:

receiving a first set of beam scan data captured at a first scan rate;

receiving a second set of beam scan data captured at a second can rate different from the first scan rate; and merging the first set of beam scan data and second set of beam scan data for form the beam scan data.

19. The optical system of claim 1, wherein the pattern is a plurality of concentric circles, wherein the visual effect comprises the plurality of concentric circles spaced apart at a variable distance, and wherein modifying at least the portion of coordinates of the coordinate map comprises modifying at least the portion of the coordinates of the coordinate map corresponding to the first surface or the second surface of the target based on the relationship between the variable distance between at least two of the plurality of concentric circles and a corresponding slope.

* * * * *